United States Patent
Purdy et al.

(10) Patent No.: US 11,172,970 B2
(45) Date of Patent: Nov. 16, 2021

(54) HIGH-PRESSURE SYRINGE WITH PRESSURE REDUCTION

(71) Applicant: DFine, Inc., South Jordan, UT (US)

(72) Inventors: Craig Purdy, Sunnyvale, CA (US); Eron Flory, Los Gatos, CA (US); David J. Johnson, San Jose, CA (US); Nate Shirley, Pleasant Grove, UT (US)

(73) Assignee: DFine, Inc., South Jordan, UT (US)

( * ) Notice: Subject to any disclaimer, the term of this patent is extended or adjusted under 35 U.S.C. 154(b) by 0 days.

(21) Appl. No.: 16/745,172

(22) Filed: Jan. 16, 2020

(65) Prior Publication Data

US 2020/0229855 A1 Jul. 23, 2020

Related U.S. Application Data

(60) Provisional application No. 62/795,343, filed on Jan. 22, 2019.

(51) Int. Cl.
*A61B 17/88* (2006.01)
*A61B 17/56* (2006.01)

(52) U.S. Cl.
CPC ...... *A61B 17/8827* (2013.01); *A61B 17/8822* (2013.01); *A61B 2017/564* (2013.01)

(58) Field of Classification Search
CPC .......... A61B 2017/564; A61B 17/8822; A61B 17/8827; A61F 2/4601
See application file for complete search history.

(56) References Cited

U.S. PATENT DOCUMENTS

| | | | |
|---|---|---|---|
| 5,047,015 A * | 9/1991 | Foote | A61M 25/104 604/99.01 |
| 5,160,327 A | 11/1992 | Stines | |
| 7,604,618 B2 | 10/2009 | Dixon | |
| 8,627,932 B2 * | 1/2014 | Marking | F16F 9/56 188/313 |
| 9,452,279 B2 * | 9/2016 | Stevens | A61M 25/10182 |
| 2002/0113088 A1 | 8/2002 | Pierson et al. | |
| 2003/0036762 A1 | 2/2003 | Kerr et al. | |
| 2008/0105840 A1 | 5/2008 | Suzuki et al. | |
| 2015/0051543 A1* | 2/2015 | Chadwick | A61M 25/10182 604/97.02 |
| 2017/0209197 A1* | 7/2017 | Balbierz | A61B 17/8816 |

OTHER PUBLICATIONS

International Search Report dated May 20, 2020 for PCT/US2020/013943.

* cited by examiner

*Primary Examiner* — Andrew Yang
(74) *Attorney, Agent, or Firm* — Stoel Rives LLP

(57) ABSTRACT

Devices used to pressurize, depressurize, or otherwise displace fluid are disclosed. The devices may be configured as a syringe. The syringe may be configured to generate high-pressure within the syringe to inflate or deflate a medical device, such as a balloon, or to inject a substance, such as bone cement, into a bone, such as a vertebra. The syringe may include a pressure reduction mechanism used to depressurize the syringe.

19 Claims, 13 Drawing Sheets

HIGH-PRESSURE SYRINGE WITH PRESSURE REDUCTION

RELATED APPLICATIONS

This application claims priority to U.S. Provisional Application No. 62/795,343, filed on Jan. 22, 2019 and titled, "High-Pressure Syringe with Pressure Reduction," which is hereby incorporated by reference in its entirety.

TECHNICAL FIELD

The present disclosure relates generally to devices used to pressurize, depressurize, or otherwise displace fluid, particularly in medical devices. More specifically, the present disclosure relates to high-pressure devices with a pressure reduction mechanism used to pressurize, depressurize, or otherwise displace fluid along a line in order to inflate or deflate a medical device, such as a balloon, or to inject a substance, such as bone cement, into a bone, such as a vertebra.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
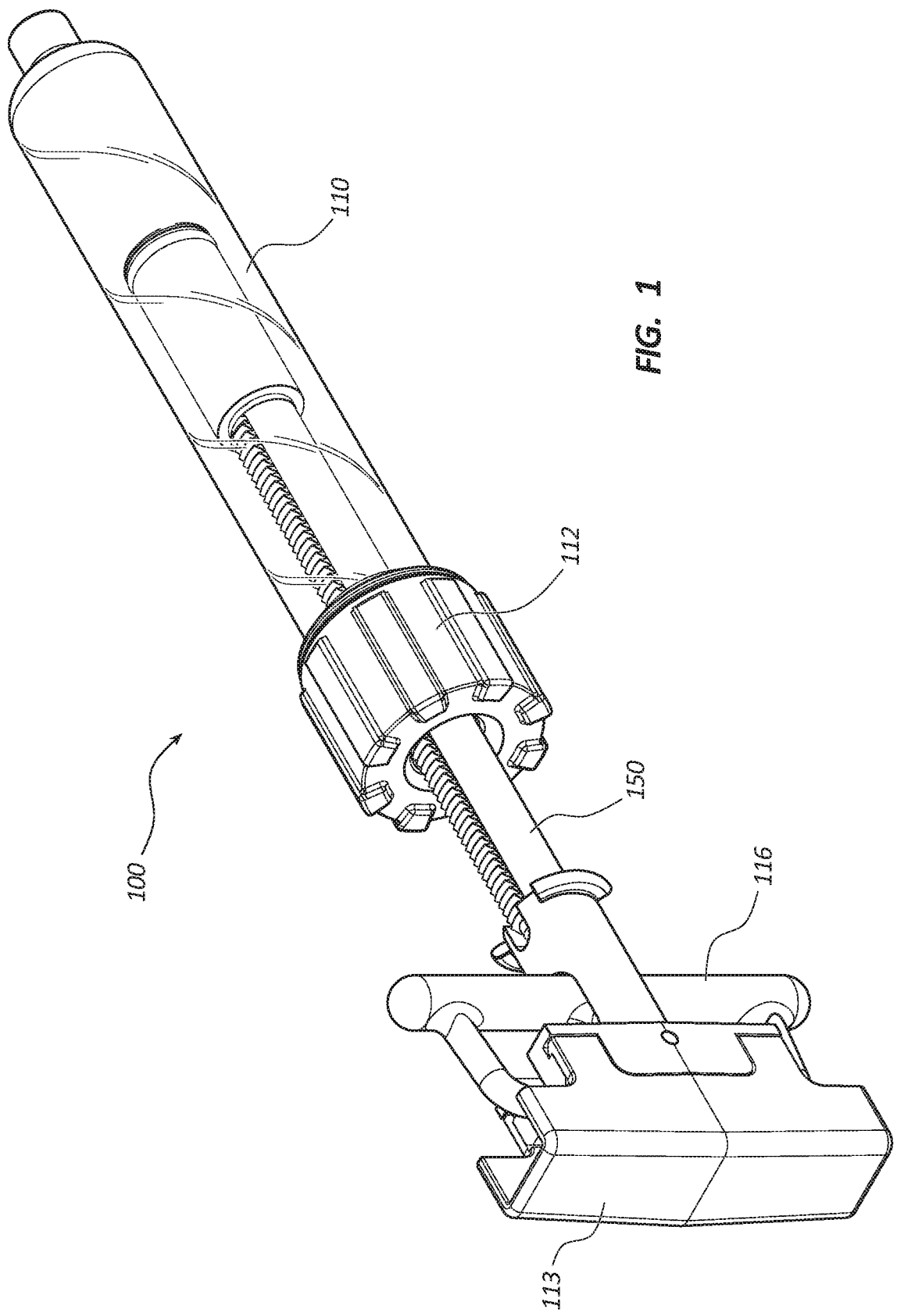
FIG. 1 is a perspective view of a high-pressure syringe with a pressure relief mechanism.

A high-pressure syringe may utilize threads to advance or retract a plunger by rotating the plunger handle relative to the barrel of the syringe such that the threads cause longitudinal displacement of the plunger relative to the body. In some instances, a high-pressure syringe may further include retractable threads, enabling a practitioner to disengage the threads and displace the plunger by simply pushing or pulling the plunger.

The high-pressure syringe may comprise a coupling member configured to constrain movement of the plunger within the syringe barrel. The coupling member may comprise threads configured to engage with the retractable threads. Certain high-pressure syringes include a mechanism in the handle of the device that allows the practitioner to disengage the threads through manipulating the mechanism. For example, in some instances the handle of such a syringe may include a "trigger" portion that may be configured to retract threads positioned on the plunger to disengaging the threads from the coupling member and allow for longitudinal displacement of the plunger.

A high-pressure syringe may be used by a practitioner for a variety of therapies, such as to inflate a balloon at an end of a catheter to expand a bone cavity or to inject a substance, such as bone cement, into a bone, such as a vertebra, to fill bone fractures.

In some embodiments, a high-pressure syringe may comprise a pressure relief mechanism to quickly reduce fluid pressure within the syringe to avoid over-pressurization of a balloon and/or to prevent injection of an excess amount of bone cement. For example, in some instances over-pressurization of a balloon may cause the balloon to burst which, in turn, may lead to tissue damage. Additionally, in therapies where the high-pressure syringe is utilized to inject bone cement into a cavity, injection of an excess amount of bone cement that may result in the bone cement leaking from the bone fractures and damaging soft tissue surrounding the bone. Thus, pressure relief mechanisms may be configured to facilitate control of fluid displacement to prevent injury to a patient.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the barrel portion of a high-pressure syringe, the proximal end of the barrel refers to the end nearest the handle and the distal end refers to the opposite end, the end nearest the inlet/outlet port of the barrel. Thus, if at one or more points in a procedure a physician changes the orientation of a barrel, as used herein, the term "proximal end" always refers to the handle end of the barrel (even if the distal end is temporarily closer to the physician).

"Fluid" is used in its broadest sense, to refer to any fluid, including both liquids and gases as well as solutions, compounds, suspensions, etc., that generally behave as fluids.

FIGS. 1-9B illustrate different views of embodiments of inflation devices and related components. In some views only selected components are illustrated, to provide detail into the relationship of the components. Some components may be shown in multiple views but not discussed in connection with every view. Disclosure provided in connection with any figure is relevant and applicable to disclosure provided in connection with any other figure or embodiment.

FIGS. 1-5C depict one embodiment of a high-pressure syringe 100. In the illustrated embodiment, the high-pressure syringe 100 comprises a syringe barrel or reservoir 110, a handle 113, a trigger 116, a rack nut 112, and a high-pressure generation member or plunger 150.

The syringe barrel 110 may be formed of a generally cylindrical hollow tube configured to receive the plunger 150. The syringe barrel 110 may include an inlet/outlet port 111 located adjacent a distal end of the syringe barrel 110. In some embodiments, the rack nut 112 may be fixedly coupled to the syringe barrel 110 adjacent a proximal end. The rack nut 112 may include a center aperture configured to allow the plunger 150 to pass through the rack nut 112 into the syringe barrel 110. Further, the rack nut 112 may include rack nut threads 119 configured to selectively couple the rack nut 112 to the plunger 150. For example, the rack nut 112 may comprise a polymeric nut at the proximal end of the syringe barrel 110. The rack nut 112 may be threadably coupled to the syringe barrel 110. In other embodiments, the rack nut 112 may be coupled to the syringe barrel 110 using any suitable technique, such as gluing, welding, overmolding, press fit, and so forth.

The plunger 150 may be configured to be longitudinally displaceable within the syringe barrel 110. The plunger 150 may be comprised of a plunger shaft coupled to a plunger seal 157 at the distal end of the plunger shaft. The plunger seal 157 may be threadably coupled to the plunger shaft. In some embodiments, the plunger seal 157 may be coupled to the plunger shaft using any suitable technique. For example, the plunger seal 157 may be coupled to the plunger shaft using techniques such as press fit, overmolding, welding, and so forth. As illustrated in FIG. 2A, the plunger seal 157 may include a plunger seal O-ring 158 that may be configured to seal against an inner surface of the syringe barrel 110. The plunger shaft may also be coupled to the handle 113 at a proximal end of the plunger shaft, with the plunger shaft spanning the distance between the plunger seal 157 and the handle 113.

The handle 113 broadly refers to the group of components coupled to the proximal end of the plunger 150, some of which may be configured to be graspable by a user. In certain embodiments, the handle 113 may be configured such that the user may manipulate the position of the plunger 150 by manipulating the handle 113. Further, in some embodiments, the handle 113 may be an actuator mechanism configured to manipulate components of the high-pressure syringe 100.

Figure 2:
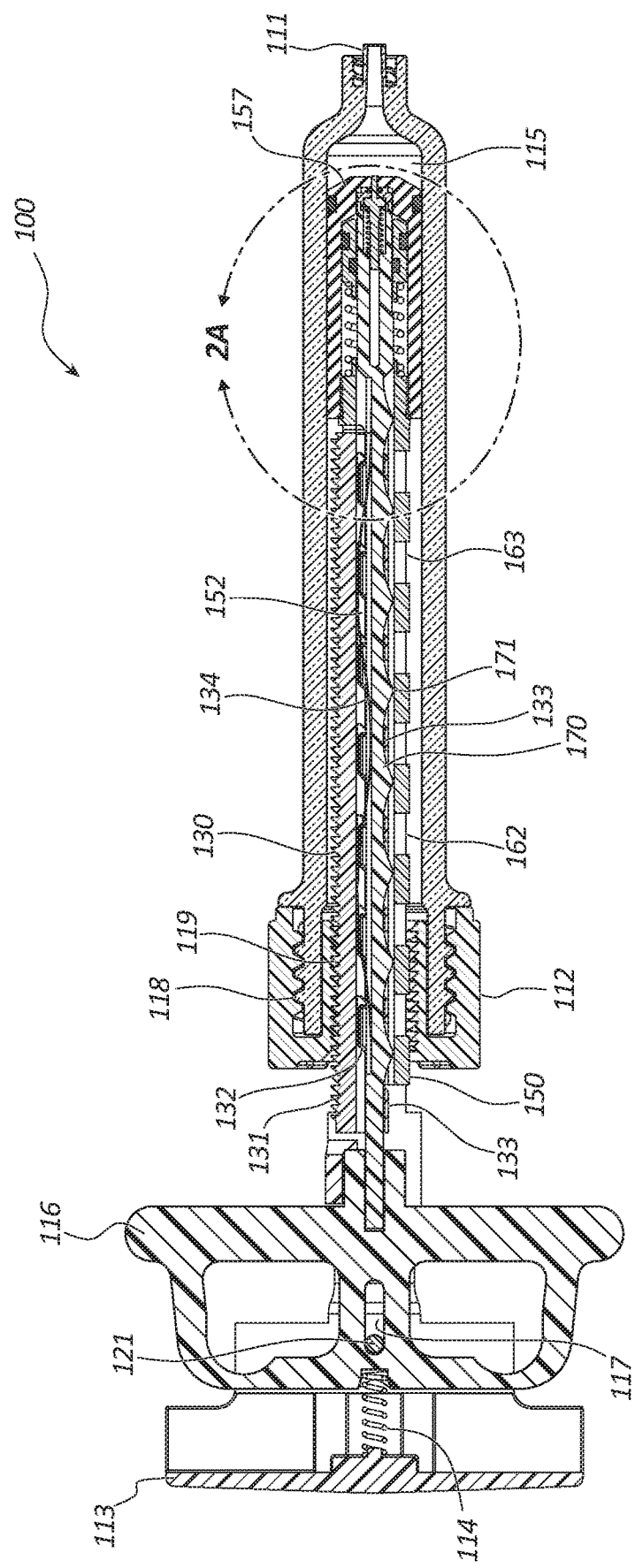
FIG. 2 is a side cross-sectional view of the high-pressure syringe of FIG. 1.
Figure 2A:
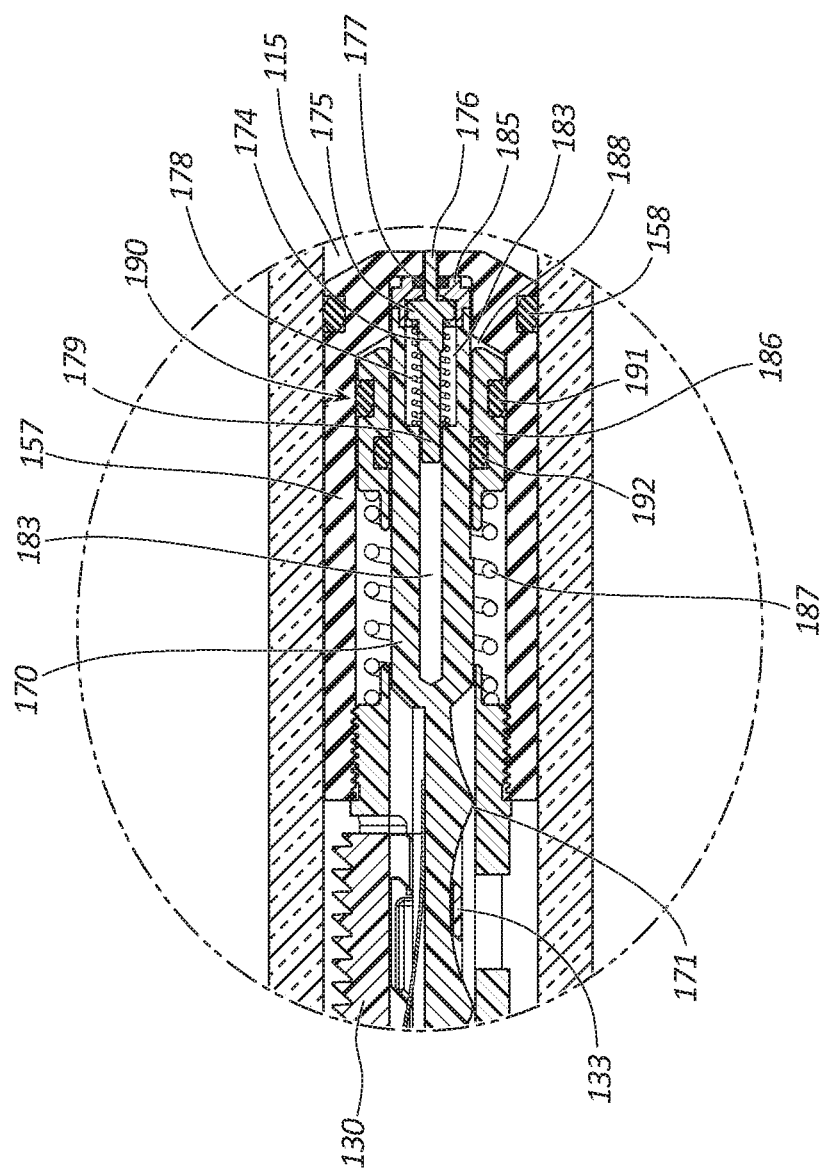
FIG. 2A is a detailed side cross-sectional view of section 2A of FIG. 2.

As shown in FIG. 2, a distal chamber 115 may be defined by the space enclosed by the inside walls of the syringe barrel 110 between the plunger seal 157 and the distal end of the syringe barrel 110. Accordingly, movement of the plunger seal 157 with respect to the syringe barrel 110 alters the size and volume of the distal chamber 115.

Figure 3:
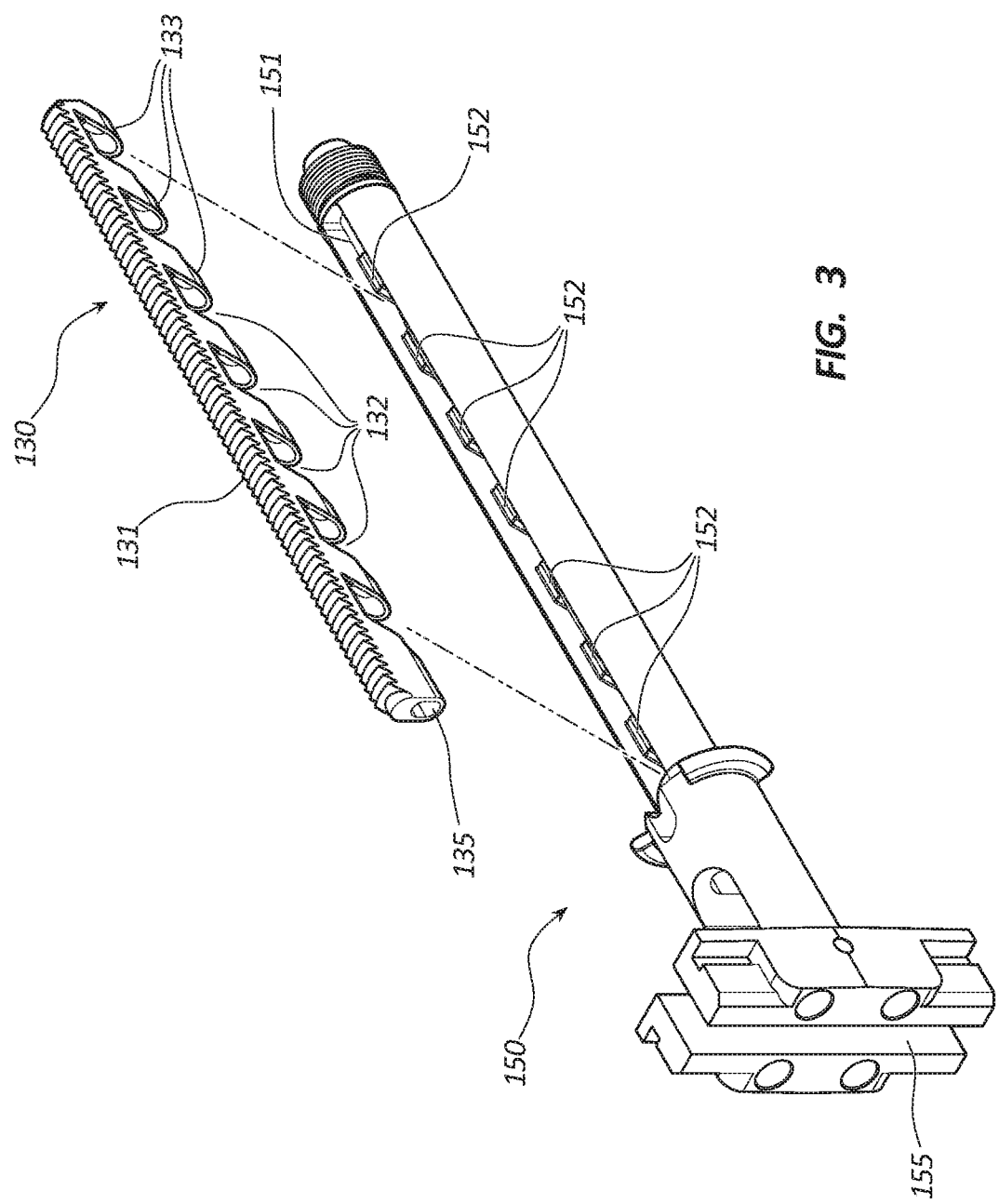
FIG. 3 is a perspective view of plunger and threaded rack components of the high-pressure syringe of FIG. 1.

As illustrated in FIGS. 2-3, in the depicted embodiment, the plunger 150 includes a U-shaped channel 151 extending along a longitudinal axis with openings at both the proximal and distal ends of the U-shaped channel 151 configured for passage of a connecting rod 170. Angled ramps 152 are disposed on both sides of the U-shaped channel 151. The angled ramps 152 are angled distally at an angle ranging from 30 to 60 degrees, including angles of 45 degrees, 40 degrees, 50 degrees, angles from 30 to 40 degrees, from 40 to 50 degrees, from 50 to 60 degrees, and from 40 to 45 degrees. The proximal end of the plunger 150 may be configured to be coupled to the handle 113. The proximal end may include a slot 155 to slidably receive the trigger 116. The bottom of the U-shaped channel 151 may include gaps 162 and struts 163.

In the embodiment of FIGS. 2-3, a threaded rack 130 is moveably disposed within the U-shaped channel 151. The threaded rack 130 includes a plurality of external rack threads 131 disposed along a longitudinal axis. The rack threads 131 may be configured to engage with the internal threads 119 of the rack nut 112. The plunger 150 may thus be translated longitudinally with respect to the syringe barrel 110 by rotating the plunger 150 such that the interaction of the rack nut threads 119 and the rack threads 131 results in the longitudinal translation of the plunger 150. Such rotating motion may be achieved when a practitioner grasps the handle 113 and rotates it clockwise to extend the plunger 150 distally or counter-clockwise to retract the plunger 150 proximally relative to the syringe barrel 110.

As also shown in FIGS. 2-3, the threaded rack 130 may include angled protrusions 132 extending from the rack threads 131. The protrusions 132 may be configured to be disposed between the angled ramps 152 and to slidably engage with the angled ramps 152. The angle of the protrusions 132 may substantially match the angle of the angled ramps 152, as discussed previously.

Figure 4:
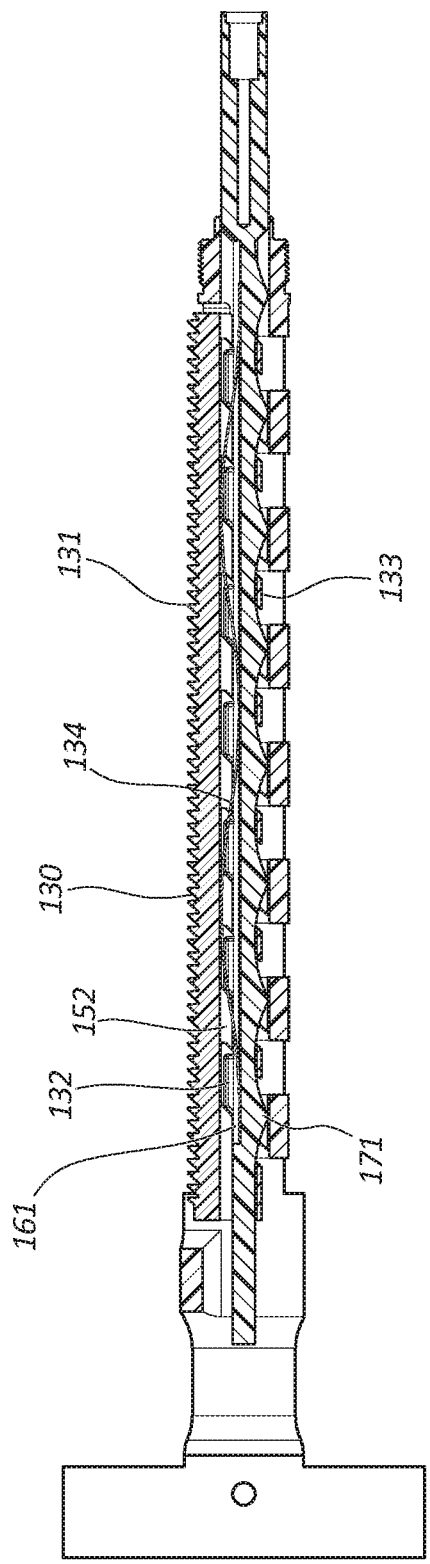
FIG. 4 is a side cross-sectional view of plunger, connecting rod, and threaded rack components of the high-pressure syringe of FIG. 1.

As illustrated in FIGS. 2-4, a connecting rod 170 may be disposed within a through bore 135 of the threaded rack 130 such that a proximal end extends proximally and a distal end extends distally from the through bore 135. The proximal end may be fixedly coupled to the trigger 116. The connecting rod 170 comprises cam lobes 171 disposed on one side along the longitudinal axis. The cam lobes 171 may be configured to engage with cam lobe receivers 133 of the angled protrusions 132 of the threaded rack 130. Longitudinal translation of the connecting rod 170 may cause the cam lobes 171 to engage with the cam lobe receivers 133. The engagement may force the cam lobe receivers 133 and the threaded rack 130 radially inward, resulting in disengagement of the rack threads 131 from the rack nut threads 119. A wave spring 134 is shown disposed in a channel 161 of the connecting rod 170. The wave spring 134 may exert a radially outwardly directed force on the threaded rack 130 to facilitate engagement of the rack threads 131 with the rack nut threads 119 when the cam lobes 171 are not engaged with the cam lobe receivers 133.

FIGS. 2-2A show a proximal portion of the connecting rod 170 comprising a pressure relief mechanism 190 disposed within a cavity of the plunger seal 157. The pressure relief mechanism 190 includes a needle valve 174, a needle valve spring 178, a pressure relief plunger 186, and a pressure relief plunger spring 187. The needle valve 174 is disposed within a connecting rod cavity 183 of the distal portion of the connecting rod 170. The needle valve 174 may include a needle valve nose 176, a needle valve flange 175, a needle valve O-ring 177, and a needle valve shaft 179. The needle valve 174 may be retained within the connecting rod cavity 183 by an end cap 185 coupled to the distal end of the connecting rod 170. The end cap 185 may also retain the needle valve O-ring 177.

FIGS. 2-2A depict the pressure relief mechanism 190 in a closed state. As illustrated, the needle valve nose 176 extends through the needle valve O-ring 177 and an aperture in the end cap 185. The needle valve O-ring 177 can seal against the needle valve nose 176 to prevent fluid from entering the connecting rod cavity 183 and a proximal or pressure relief chamber 188 within the cavity of the plunger seal 157. The needle valve nose 176 may also extend through an aperture in the plunger seal 157. A distal end of the needle valve nose 176 may be flush with a distal surface of the plunger seal 157. In another embodiment, the distal end of the needle valve nose 176 may extend distally beyond the distal surface of the plunger seal 157.

The needle valve shaft 179 may be slidably received within a smaller diameter and proximal portion of the connecting rod cavity 183. The needle valve spring 178 may surround the needle valve shaft 179 and be disposed between the needle valve flange 175 and a shoulder of the connecting rod cavity 183. The needle valve spring 178 may be configured to apply a distally directed force to the needle valve 174 in the closed state.

The pressure relief plunger 186 is shown disposed around the distal portion of the connecting rod 170. The pressure relief plunger 186 may comprise an external O-ring 191 configured to seal the pressure relief plunger 186 against an inside surface of the cavity of the plunger seal 157 and an internal O-ring 192 configured to seal the pressure relief plunger 186 against an outer surface of the distal portion of the connecting rod 170. The pressure relief plunger 186 may be configured to translate proximally when fluid presses against a proximal end to expand the proximal chamber 188 within the cavity of the plunger seal 157.

The needle valve spring 178 may be configured to maintain the needle valve 174 in the closed state until the fluid pressure within the syringe barrel 110 exceeds a safety pressure level. In some instances, the safety pressure level may be exceeded when the high-pressure syringe 100 is used by a physician to expand a balloon within a bone cavity or when injecting bone cement into a bone cavity. In other instances, the high-pressure syringe 100 may be shipped and stored with fluid in the distal chamber 115. Environmental conditions, such as heat or cold, may cause the fluid to expand and increase the fluid pressure within the distal chamber 115. When the safety pressure level is exceeded, fluid may exert a proximally directed force on the needle valve nose 176 causing the needle valve 174 to translate proximally and the needle valve spring 178 to compress to open the needle valve 174 such that fluid flows from the distal chamber 115 into the proximal chamber 188.

The fluid may also force the pressure relief plunger 186 to move proximally to expand the volume of the proximal chamber 188. When the fluid flows into the proximal chamber 188 the fluid pressure may be reduced within the distal chamber 115. When the fluid pressure within the distal chamber 115 drops below the safety level, the pressure relief plunger spring 187 may exert a distally directed force on the pressure relief plunger 186, causing the fluid within the proximal chamber 188 to be expelled into the syringe barrel 110. Additionally, the needle valve spring 178 may exert a distally directed force on the needle valve 174 to translate the needle valve 174 distally and close the pressure relief mechanism 190.

FIG. 2 illustrates a trigger 116 operatively coupled to the handle 113 on a proximal portion and fixedly coupled to the connecting rod 170 at a distal portion. The trigger 116 comprises a longitudinally oriented slot 117. A pin 121 may extend through the handle 113 and the slot 117 to allow the trigger 116 to translate proximally and distally relative to the handle 113. The trigger 116 may be of any suitable form to allow the user to grasp the trigger 116 and displace the trigger 116 proximally toward the handle 113. A handle spring 114 is shown disposed between the trigger 116 and a proximal wall of the handle 113. The handle spring 114 may be configured to apply a distally directed force to the trigger 116 and the connecting rod 170 to maintain the pressure relief mechanism 190 in the closed state.

The trigger 116, when proximally displaced by the user, may be configured to reduce fluid pressure within the syringe barrel 110 and to disengage the rack threads 131 from the nut threads 119 to allow the plunger 150 to be freely translated by the user. The trigger 116 may be configured to displace the connecting rod 170 proximally. Proximal displacement of the connecting rod 170 may translate the pressure relief mechanism 190 proximally. Upon proximal translation of the pressure relief mechanism 190, the nose 176 of the needle valve 174 may be pulled from the aperture in the plunger seal 157 to allow fluid from the distal chamber 115 to flow into the proximal chamber 188. As fluid flows into the proximal chamber 188, the pressure relief plunger 186 may be displaced proximally and the pressure relief plunger spring 187 may be compressed. The flow of fluid from the distal chamber 115 to the proximal chamber 188 may reduce the fluid pressure within the distal chamber 115.

Additionally, proximal translation of the connecting rod 170 causes the cam lobes 171 to engage with the cam lobe receivers 133. The threaded rack 130 may be displaced radially inwardly and proximally to reduce the engagement force of the rack threads 131 and the nut threads 119 to permit easy disengagement.

The high-pressure syringe 100 may be fluidly coupled to a bone cement delivery syringe. The bone cement delivery syringe may be fluidly coupled to a delivery device that has been inserted into a fractured bone, such as a vertebra. The bone cement may be configured to fill the bone fractures and add strength to the bone. The bone cement may begin curing and increasing in viscosity within the bone cement delivery syringe, resulting in a need to generate high pressures within the high-pressure syringe 100 in order to allow for a longer working time. The bone cement delivery pressures may be as high as 90 atmospheres within the high-pressure syringe 100. In some instances, a clinician may desire to terminate delivery of the bone cement immediately upon visualizing the complete filling of a bone fracture to avoid seepage of the bone cement from the fracture into surrounding soft tissue.

In some instances, a cavity may be formed within the vertebra prior to injecting bone cement. The cavity may be formed by a high-pressure balloon catheter inserted into the vertebra using a kyphoplasty or vertebroplasty procedure. The high-pressure balloon catheter may be fluidly coupled to a high-pressure syringe. The high-pressure balloon may be expanded under pressures up to and including 60 atmospheres, 55 atmospheres, 50 atmospheres, or more, generated by the high-pressure syringe. Additionally, the clinician may desire to immediately reduce the pressure within the balloon to avoid balloon rupture or leakage.

Figure 5A:
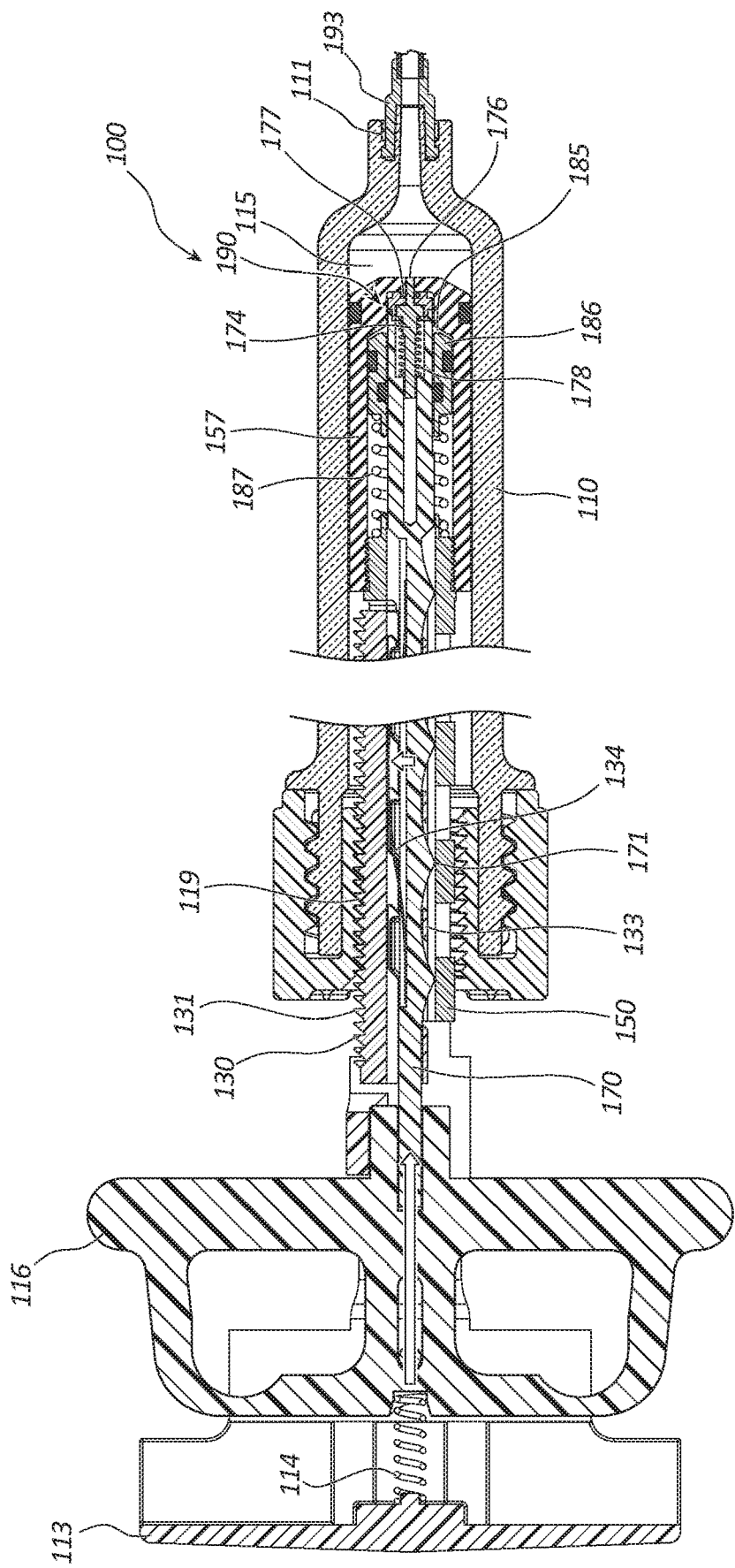
FIG. 5A is a side cross-sectional view of the high-pressure syringe of FIG. 1 with a pressure relief mechanism in a closed state.
Figure 5B:
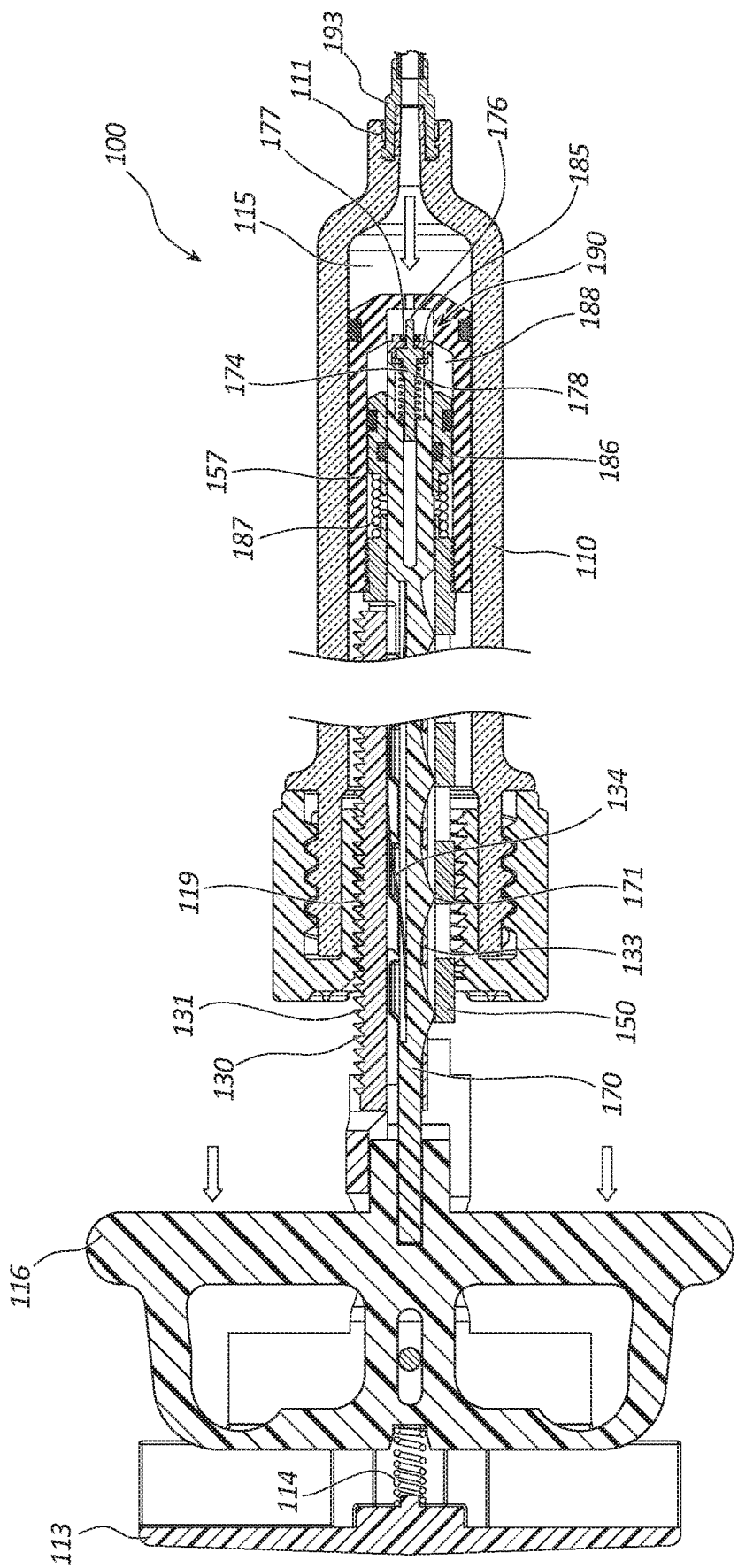
FIG. 5B is a side cross-sectional view of the high-pressure syringe of FIG. 1 in a pressure relief state.
Figure 5C:
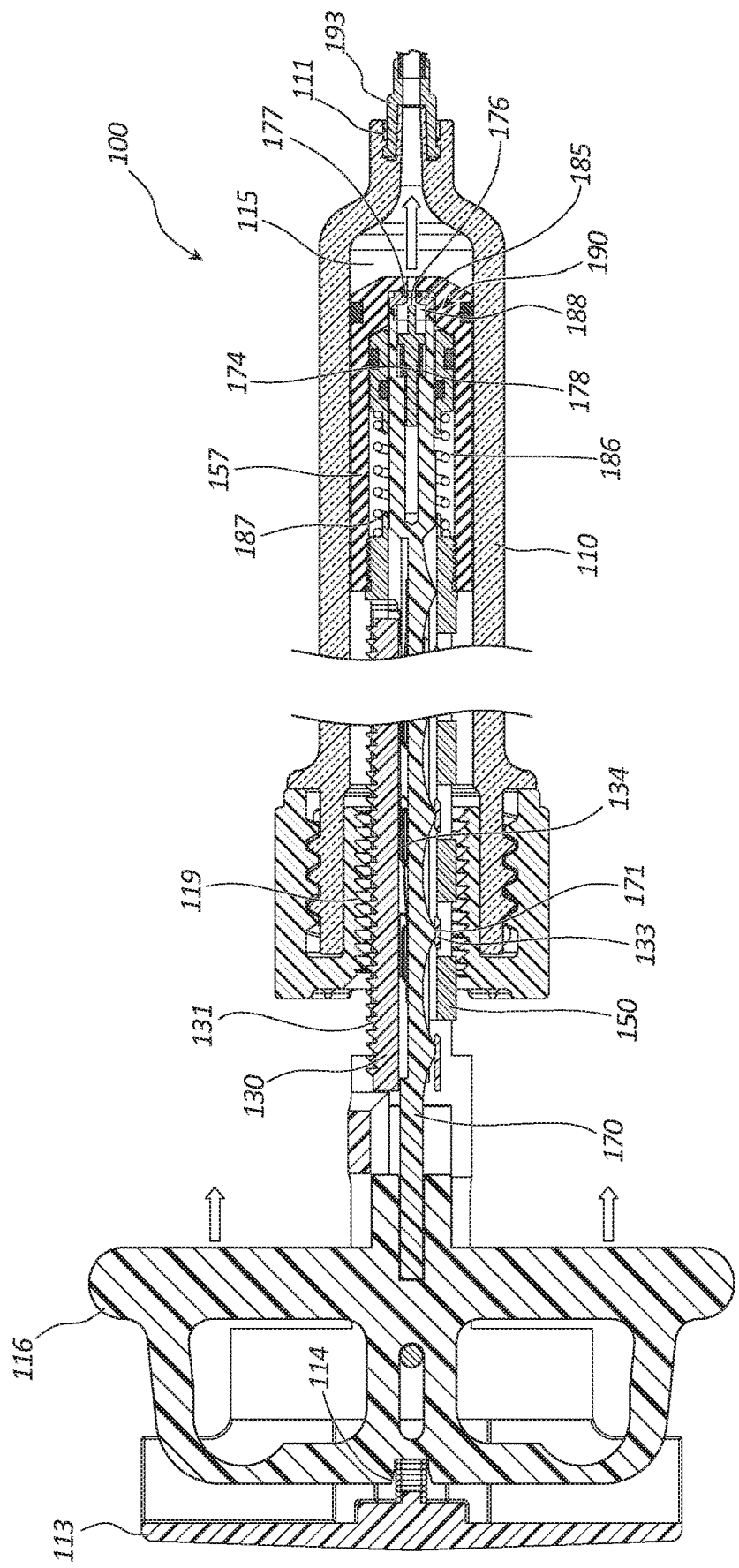
FIG. 5C is a side cross-sectional view of the high-pressure syringe of FIG. 1 in a fluid return state.
Figure 6:
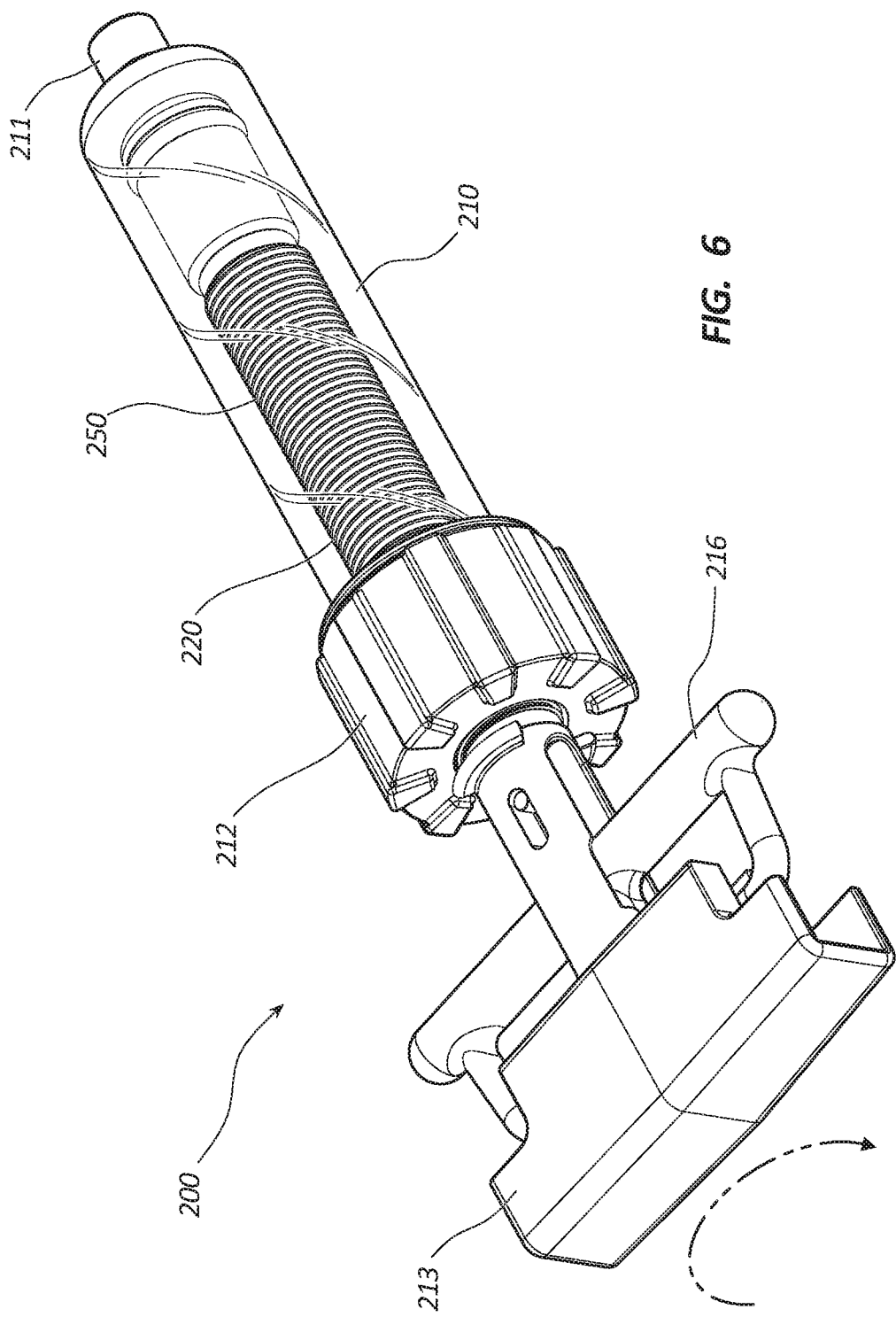
FIG. 6 is a perspective view of another embodiment of a high-pressure syringe with a pressure relief mechanism.

FIGS. 5A-5C illustrate the high-pressure syringe 100 in use. FIG. 5A depicts the high-pressure syringe 100 in a ready state. A fluid connector 193 is fluidly coupled to the inlet/outlet port 111 of the syringe barrel 110. The fluid connector 193 may be coupled to a bone cement delivery syringe (not shown) at a distal end. In another embodiment, the fluid connector 193 may be fluidly coupled to a balloon catheter (not shown) at the distal end. Fluid, such as saline, may fill the distal chamber 115 and the fluid connector 193. The plunger 150 and the plunger seal 157 may be disposed within the syringe barrel 110. The pressure relief mechanism 190 may be in a closed state. The connecting rod 170 may be distally positioned such that the end cap 185 and the needle valve O-ring 177 may be pressed against an inner surface of the plunger seal 157. The needle valve nose 176 may extend through the aperture in the plunger seal 157. The cam lobes 171 may be disengaged from the cam lobe receivers 133. The wave spring 134 may exert a radially outwardly directed force to the threaded rack 130 such that the rack threads 131 may be engaged with the nut threads 119. The handle spring 114 may apply a distally directed force to the trigger 116 such that the trigger 116 may be disposed distally of the handle 113.

The clinician may rotate the handle 113 clockwise relative to the syringe barrel 110 to translate the plunger 150 distally and to apply pressure to the fluid within the distal chamber 115. In some instances, the fluid may be pressurized due to flow resistance at the cement delivery syringe. FIG. 5B illustrates the high-pressure syringe 100 in a pressure reducing state. The trigger 116 may be displaced proximally relative to the handle 113 by the physician. The handle spring 114 may be compressed by the trigger 116. The connecting rod 170 may be proximally translated. The pressure relief mechanism 190 may be proximally displaced such that the end cap 185 and the needle valve O-ring 177 may be disposed away from the internal surface of the plunger seal 157. The needle valve nose 176 may be pulled from the aperture in the plunger seal 157 to allow fluid to flow from the distal chamber 115 into the proximal chamber 188. The pressure relief plunger 186 may be displaced proximally by the fluid such that the volume of the proximal chamber 188 is increased. The pressure relief plunger spring 187 may be compressed. The fluid volume and pressure within the distal chamber 115 and the bone cement delivery syringe may be reduced which may result in an immediate stop of bone cement flow into the vertebra. The cam lobes 171 may be partially engaged with the cam lobe receivers 133. The threaded rack 130 may be partially displaced proximally and radially inward such that the rack threads 131 may be partially disengaged from the nut threads 119. In some embodiments, the reduction in pressure within the distal chamber 115 facilitated by the pressure relief mechanism 190 may provide for an improved user experience (e.g., reduced force needed to activate the trigger and reduction or elimination of loud noise or pop when the rack threads 131 are disengaged from the nut threads 119). In other embodiments, the reduction in pressure within the distal chamber 115 may reduce or eliminate damage to the rack threads 131 and/or the nut threads 119 during disengagement.

FIG. 5C shows the high-pressure syringe 100 in a fluid return state. The cam lobes 171 may be fully engaged with the cam lobe receivers 133 such that the threaded rack 130 may be fully displaced proximally and radially inwardly. The rack threads 131 may be fully disengaged from the nut threads 119 such that the plunger 150 is freely moveable relative to the distal chamber 115. This may allow for a further reduction of pressure within the distal chamber 115. Upon reduction of fluid pressure within the distal chamber 115, the pressure relief plunger 186 may be displaced distally by the pressure relief plunger spring 187 to push fluid from the proximal chamber 188 into the distal chamber 115. The clinician may release the trigger 116 to allow the handle spring 114 to exert a distally directed force on the trigger 116 and the connecting rod 170. The trigger 116 and the connecting rod 170 may be translated distally such that substantially all fluid is forced from the proximal chamber 188 and the pressure relief mechanism 190 returns to the ready state. In some embodiments, this cycle of fluid pressure generation, fluid pressure relief, and fluid return may be repeated more than 10 times, more than five times, or more than three times during a single procedure.

FIGS. 6-9B depict an embodiment of a high-pressure syringe 200 that resembles the high-pressure syringe 100 described above in certain respects. Accordingly, like features are designated with like reference numerals, with the leading digit incremented to "2." For example, the embodiment depicted in FIGS. 6-9B includes a pressure relief mechanism that may, in some respects, resemble the pressure relief mechanism 190 of FIG. 2. Relevant disclosure set forth above regarding similarly identified features thus may not be repeated hereafter. Moreover, specific features of the high-pressure syringe 100 and related components shown in FIGS. 1-5C may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the high-pressure syringe 200 and related components depicted in FIGS. 6-9B. Any suitable combination of the features, and variations of the same, described with respect to the high-pressure syringe 100 and related components illustrated in FIGS. 1-5C can be employed with the high-pressure syringe 200 and related components of FIGS. 6-9B, and vice versa.

FIGS. 6-9B depict another embodiment of a high-pressure syringe 200. In the illustrated embodiment, the high-pressure syringe 200 is partially comprised of a syringe barrel or reservoir 210, a handle 213, a trigger 216, and a high-pressure generation member or plunger 250.

The syringe barrel 210 may be formed of a generally cylindrical hollow tube configured to receive the plunger 250. The syringe barrel 210 may include an inlet/outlet port 211 located adjacent a distal end of the syringe barrel 210. In some embodiments, a plunger nut 212 may be fixedly coupled to the syringe barrel 210 adjacent a proximal end. The plunger nut 212 may include a center aperture configured to allow the plunger 250 to pass through the plunger nut 212 into the syringe barrel 210. Further, the plunger nut 212 may include plunger nut threads 219 configured to couple the plunger nut 212 to the plunger 250. For example, the plunger nut 212 may comprise a polymeric nut at the proximal end of the syringe barrel 210. The plunger nut 212 may be threadably coupled to the syringe barrel 210. In other embodiments, the plunger nut 212 may be coupled to the syringe barrel 210 using any suitable technique, such as gluing, welding, overmolding, press fit, and so forth.

The plunger 250 may be configured to be longitudinally displaceable within the syringe barrel 210. The plunger 250 may be comprised of a plunger shaft coupled to a plunger seal 257 at a distal end. Plunger threads 241 may circumscribe at least a portion of the plunger shaft. The plunger threads 241 may be configured to engage with or mesh with the plunger nut threads 219 to axially translate during rotation of the plunger 250. The plunger seal 257 may be threadably coupled to a distal end of the plunger shaft. In some embodiments, the plunger seal 257 may be coupled to the plunger shaft using any suitable technique. For example, the plunger seal 257 may be coupled to the plunger shaft using techniques such as press fit, overmolding, welding, and so forth. As illustrated in FIG. 7A, the plunger seal 257 may include an external plunger seal O-ring 258 that may be configured to seal against an inner surface of the syringe barrel 210 and an internal plunger seal O-ring 260 that may be configured to seal against the plunger 250. The plunger shaft may also be fixedly coupled to the handle 213 at the proximal end of the plunger shaft, with the plunger shaft spanning the distance between the plunger seal 257 and the handle 213.

The handle 213 broadly refers to the group of components coupled to the proximal end of the plunger 250, some of which may be configured to be graspable by a user. In certain embodiments, the handle 213 may be configured such that the user may manipulate the position of the plunger 250 by manipulating the handle 213. Further, in some embodiments, the handle 213 may be an actuator mechanism configured to manipulate components of the high-pressure syringe 200.

A handle configured to provide a mechanical advantage rotating the plunger 250 may be desirable for certain therapies that require large syringes or high pressure. Such therapies may also require a larger biasing force due to the size of the device or the pressure within the device. A handle providing a mechanical advantage may make devices configured for such therapies easier to use. Such a handle may include an extendable crank.

Figure 7:
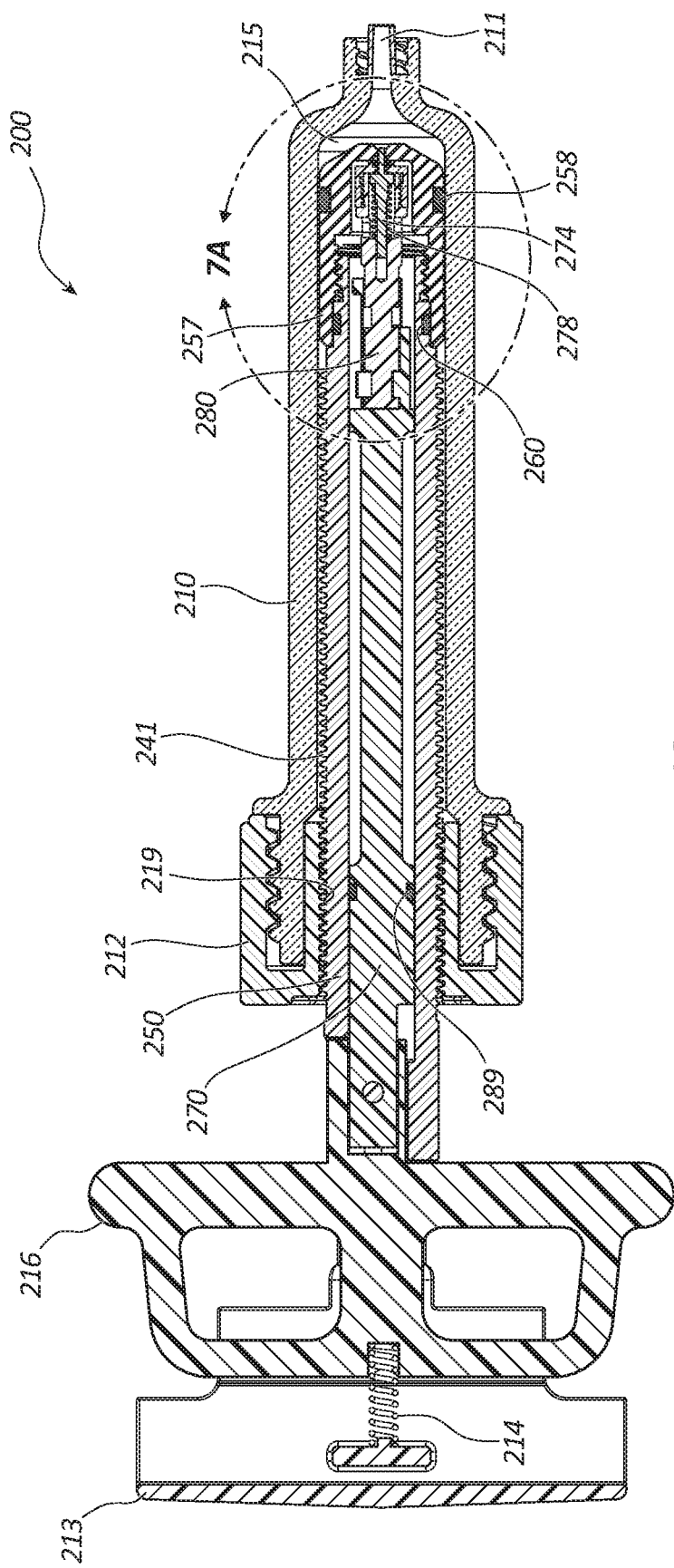
FIG. 7 is a side cross-sectional view of the high-pressure syringe of FIG. 6.
Figure 7A:
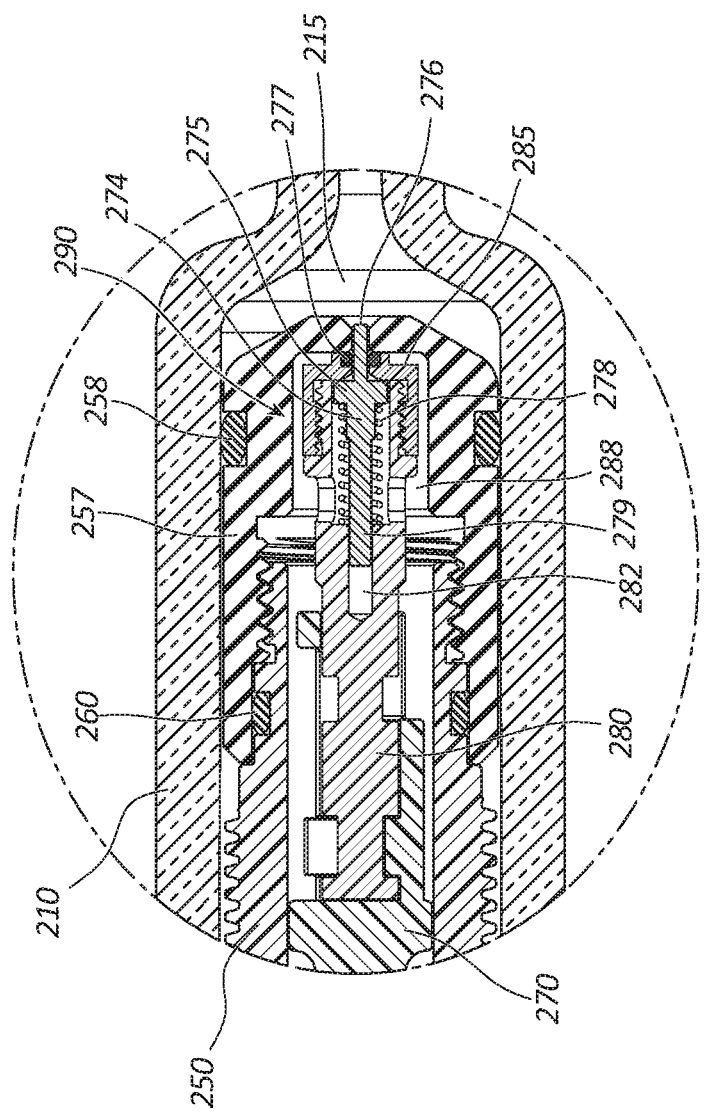
FIG. 7A is a detailed side cross-sectional view of section 7A of FIG. 7.

As shown in FIGS. 7-7A, a distal chamber 215 may be defined by the space enclosed by the inside walls of the syringe barrel 210 between the plunger seal 257 and the distal end of the syringe barrel 210. Accordingly, movement of the plunger seal 257 with respect to the syringe barrel 210 will alter the size and volume of the distal chamber 215.

FIGS. 7-7A show a proximal portion of the plunger 250 comprising a pressure relief mechanism 290 disposed within a cavity of the plunger seal 257. The pressure relief mechanism 290 includes a needle valve housing 280, a needle valve 274, and a needle valve spring 278. As illustrated, the needle valve 274 is disposed within the needle valve housing 280. The needle valve housing 280 may be fixedly coupled to a proximal end of a connecting rod 270. The connecting rod 270 may be slidably disposed within a bore of the plunger 250. The needle valve 274 may include a needle valve nose 276, a needle valve flange 275, a needle valve O-ring 277, and a needle valve shaft 279. The needle valve 274 may be retained within the needle valve housing 280 by an end cap 285 coupled to a distal end of the needle valve housing 280. The end cap 285 may also retain the needle valve O-ring 277.

FIG. 7 illustrates a trigger 216 operatively coupled to the handle 213 adjacent a proximal portion and fixedly coupled to the connecting rod 270 adjacent a distal portion. The trigger 216 may be of any suitable form to allow the user to grasp the trigger 216 and displace the trigger 216 proximally toward the handle 213. A handle spring 214 is shown disposed between the trigger 216 and a proximal wall of the handle 213. The handle spring 214 may be configured to apply a distally directed force to the trigger 216 and the connecting rod 270 to maintain the pressure relief mechanism 290 in the closed state.

FIGS. 7-7A depict the pressure relief mechanism 290 in a closed state. As illustrated, the needle valve nose 276 extends through the needle valve O-ring 277 and an aperture in the end cap 285. The needle valve O-ring 277 may seal against the needle valve nose 276 to prevent fluid from entering the needle valve housing 280 and a proximal chamber 288 within the cavity of the plunger seal 257 and the plunger 250. The proximal chamber 288 may be defined by an annular space between the connecting rod 270 and an internal wall of the plunger 250 and the plunger seal 257. A connecting rod O-ring 289 may be disposed adjacent a proximal end of the connecting rod 270 and may be configured to seal a proximal end of the proximal chamber 288. The needle valve nose 276 may also extend through an aperture in the plunger seal 257. A distal end of the needle valve nose 276 may be flush with a distal surface of the plunger seal 257. In another embodiment, the distal end of the needle valve nose 276 may extend distally beyond the distal surface of the plunger seal 257.

The needle valve shaft 279 may be slidably received within a smaller diameter and proximal portion of a cavity of the needle valve housing 280. The needle valve spring 278 may surround the needle valve shaft 279 and be disposed between the needle valve flange 275 and a shoulder of the cavity of the needle valve housing 280. The needle valve spring 278 may be configured to apply a distally directed force to the needle valve 274 in the closed state. The needle valve spring 278 may be configured to maintain the needle valve 274 in the closed state until the fluid pressure within the syringe barrel 210 exceeds a safety pressure level.

Figure 8:
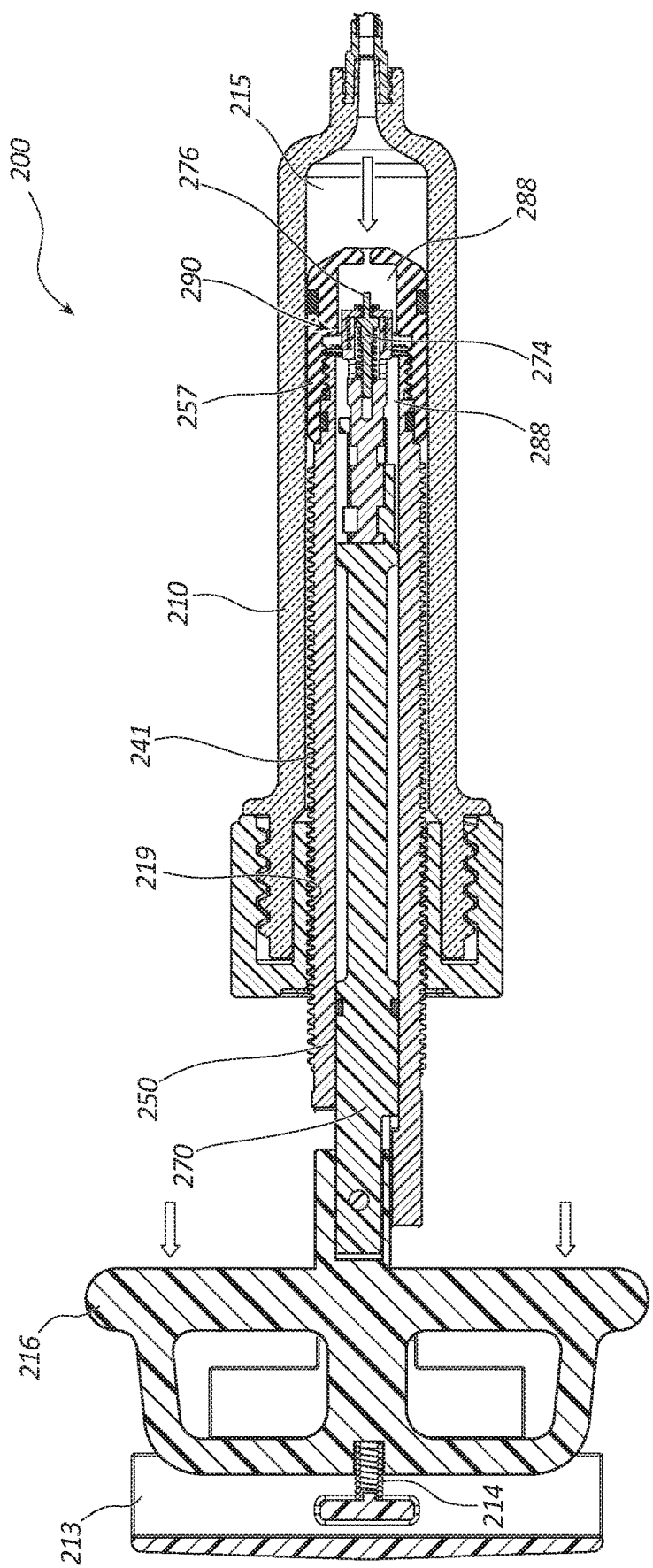
FIG. 8 is a side cross-sectional view of the high-pressure syringe of FIG. 6 in a pressure relief state.

The pressure relief mechanism 190, when proximally displaced by the user, may be configured to reduce fluid pressure within the syringe barrel 210. The trigger 216 may be configured to displace the connecting rod 270 proximally as depicted in FIG. 8. Proximal displacement of the connecting rod 270 may translate the pressure relief mechanism 290 proximally. Upon proximal translation of the pressure relief mechanism 290, the nose 276 of the needle valve 274 may be pulled from the aperture in the plunger seal 257 to allow fluid from the distal chamber 215 to flow into the proximal chamber 288. The flow of fluid from the distal chamber 215 to the proximal chamber 288 may reduce the fluid pressure within the distal chamber 215.

Figure 9B:
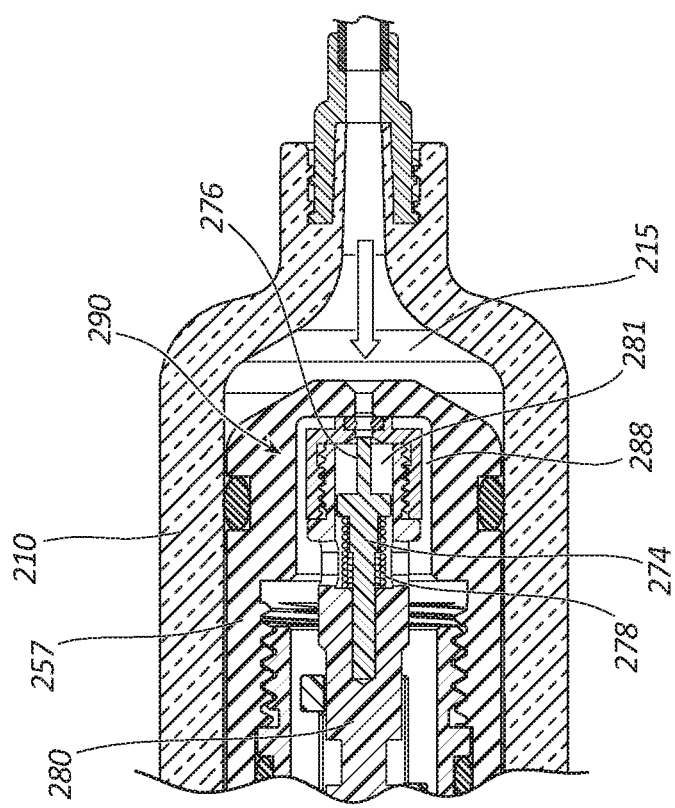
FIG. 9B is a side cross-sectional view of a portion of the high-pressure syringe of FIG. 6 in a safety pressure relief state.
Figure 9A:
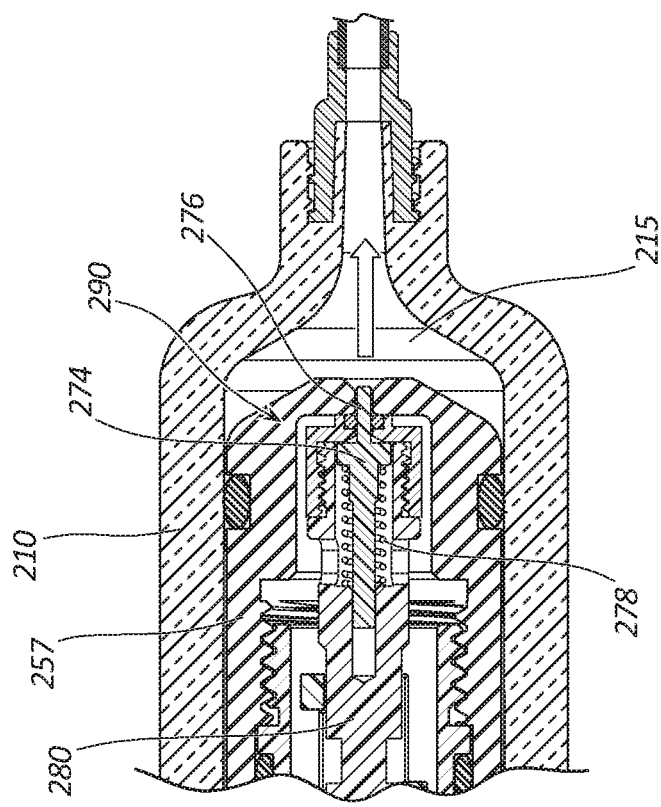
FIG. 9A is a side cross-sectional view of a portion of the high-pressure syringe of FIG. 6 in a closed state.

FIGS. 9A-9B illustrate the pressure relief mechanism 290 in a closed state (FIG. 9A) and a safety pressure relief state (FIG. 9B). When the fluid pressure level within the distal chamber 215 is exceeded, the fluid may exert a proximally directed force on the needle valve nose 276, forcing the needle valve 274 to translate proximally and the needle valve spring 278 to compress. The pressure relief mechanism 290 may transition to the safety pressure relief state, as shown in FIG. 9B, where fluid flows from the distal chamber 215 into the proximal chamber 288. When the fluid flows into the proximal chamber 288 the fluid pressure may be reduced within the distal chamber 215. When the fluid pressure within the distal chamber 215 drops below the safety level, the needle valve spring 278 may exert a distally directed force on the needle valve 274, causing the needle valve 274 to translate distally and transition the pressure relief mechanism 290 to a closed state as shown in FIG. 9A.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A high-pressure syringe, comprising:
a barrel comprising a distal chamber;
a high-pressure generation member comprising a seal, a connecting rod, and a needle valve disposed at a distal end of the connecting rod; and
a pressure relief mechanism,
wherein the seal comprises an aperture,
wherein the needle valve is configured to seal the aperture, and
wherein the connecting rod and needle valve are configured to be displaced proximally to unseal the aperture and allow fluid to flow into a proximal chamber from the distal chamber, wherein a fluid pressure within the distal chamber is reduced.

2. The high-pressure syringe of claim 1, wherein the high-pressure generation member further comprises a plunger.

3. The high-pressure syringe of claim 2, wherein the high-pressure generation member further comprises a rack having external threads and disposed within a channel of the plunger.

4. The high-pressure syringe of claim 3, wherein the external threads are configured to engage and disengage with internal threads of a nut, wherein the nut is coupled to the barrel.

5. The high-pressure syringe of claim 3, wherein the rack is configured to be radially displaced.

6. The high-pressure syringe of claim 3, wherein the connecting rod is disposed within the rack, wherein the connecting rod comprises cam lobes configured to engage with cam lobe receivers of the rack when the connecting rod is longitudinally translated, wherein the rack is radially inwardly displaced.

7. The high-pressure syringe of claim 3, further comprising a wave spring configured to exert a radial outward force on the rack.

8. The high-pressure syringe of claim 2, wherein the plunger comprises external threads configured to engage with internal threads of a nut coupled to the barrel.

9. The high-pressure syringe of claim 1, wherein the needle valve is configured to be displaced proximally to unseal the aperture and to allow fluid to flow into a proximal chamber from the distal chamber when a fluid pressure within the distal chamber exceeds a maximum allowable pressure, wherein the fluid pressure is reduced.

10. The high-pressure syringe of claim 1, wherein a pressure relief plunger is disposed within the proximal chamber and configured to be displaced proximally by the fluid within the proximal chamber, wherein the proximal chamber is expanded.

11. The high-pressure syringe of claim 10, wherein a pressure relief plunger spring applies a distally directed force to the pressure relief plunger to push fluid from the proximal chamber into the distal chamber through the aperture when the fluid pressure within the distal chamber is less than a fluid pressure within the proximal chamber, and wherein a needle valve spring applies a distally directed force to the needle valve to seal the aperture.

12. A high-pressure syringe, comprising:
a barrel comprising a distal chamber;
a high-pressure generation member comprising a plunger and a rack disposed within a channel of the plunger;
a pressure relief mechanism; and
a wave spring configured to exert a radial outward force on the rack.

13. The high-pressure syringe of claim 12, wherein the high-pressure generation member further comprises a connecting rod, wherein the connecting rod comprises a needle valve disposed at a distal end of the connecting rod, wherein the plunger comprises a plunger seal having an aperture, wherein the needle valve is configured to seal the aperture, and wherein the connecting rod and needle valve are configured to be displaced proximally to unseal the aperture and allow fluid to flow into a proximal chamber from the distal chamber, thereby reducing a fluid pressure within the distal chamber.

14. The high-pressure syringe of claim 13, wherein a pressure relief plunger is disposed within the proximal chamber and configured to be displaced proximally by the fluid within the proximal chamber, thereby expanding the proximal chamber.

15. The high-pressure syringe of claim 14, wherein a pressure relief plunger spring applies a distally directed force to the pressure relief plunger to push fluid from the proximal chamber into the distal chamber through the aperture when the fluid pressure within the distal chamber is less than a fluid pressure within the proximal chamber, and wherein a needle valve spring applies a distally directed force to the needle valve to seal the aperture.

16. A high-pressure syringe, comprising:
a barrel comprising a distal chamber;
a high-pressure generation member comprising a proximal chamber and a seal disposed between the proximal chamber and the distal chamber, the seal having an aperture; and
a pressure relief mechanism comprising a connecting rod coupled to a needle valve, the needle valve configured to seal the aperture,
wherein the seal is selectively openable in response to a user input, wherein the user input displaces the connecting rod to pull the needle valve from the aperture.

17. The high-pressure syringe of claim 16, wherein the connecting rod and needle valve are configured to be displaced proximally to unseal the aperture and allow fluid to flow into the proximal chamber from the distal chamber, thereby reducing a fluid pressure within the distal chamber.

18. The high-pressure syringe of claim 17, wherein a pressure relief plunger is disposed within the proximal chamber and configured to be displaced proximally by the fluid within the proximal chamber, thereby expanding the proximal chamber.

19. The high-pressure syringe of claim 18, wherein a pressure relief plunger spring applies a distally directed force to the pressure relief plunger to push fluid from the proximal chamber into the distal chamber through the aperture when the fluid pressure within the distal chamber is less than a fluid pressure within the proximal chamber, and wherein a needle valve spring applies a distally directed force to the needle valve to seal the aperture.

* * * * *